(12) United States Patent
Xu et al.

(10) Patent No.: US 7,777,013 B2
(45) Date of Patent: *Aug. 17, 2010

(54) LABELED NUCLEOTIDE ANALOGS AND USES THEREFOR

(75) Inventors: Yue Xu, Fremont, CA (US); Jeffrey Wegener, Cupertino, CA (US); Arek Bibillo, Cupertino, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 144 days.

This patent is subject to a terminal disclaimer.

(21) Appl. No.: 12/121,641

(22) Filed: May 15, 2008

(65) Prior Publication Data

US 2009/0018324 A1 Jan. 15, 2009

Related U.S. Application Data

(63) Continuation of application No. 11/241,809, filed on Sep. 29, 2005, now Pat. No. 7,405,281.

(51) Int. Cl.
*C07G 11/00* (2006.01)
*C07H 21/00* (2006.01)
*C07H 21/02* (2006.01)
*C07H 19/04* (2006.01)

(52) U.S. Cl. .................. 536/4.1; 536/23.1; 536/25.33; 536/25.34; 536/26.6

(58) Field of Classification Search .............. 536/4.1, 536/23.1, 25.33, 25.34, 26.6
See application file for complete search history.

(56) References Cited

U.S. PATENT DOCUMENTS

| 5,547,839 | A | 8/1996 | Dower et al. |
|---|---|---|---|
| 5,610,289 | A | 3/1997 | Cook et al. |
| 5,688,648 | A | 11/1997 | Mathies et al. |
| 5,821,058 | A | 10/1998 | Smith et al. |
| 6,210,896 | B1 | 4/2001 | Chan |
| 6,399,335 | B1 | 6/2002 | Kao et al. |
| 6,664,079 | B2 | 12/2003 | Ju et al. |
| 6,818,395 | B1 | 11/2004 | Quake et al. |
| 6,869,764 | B2 | 3/2005 | Williams et al. |
| 6,982,146 | B1 | 1/2006 | Schneider et al. |
| 7,033,762 | B2 | 4/2006 | Nelson et al. |
| 7,033,764 | B2 | 4/2006 | Korlach et al. |
| 7,041,812 | B2 | 5/2006 | Kumar et al. |
| 7,052,847 | B2 | 5/2006 | Korlach et al. |
| 7,056,661 | B2 | 6/2006 | Korlach et al. |
| 7,056,676 | B2 | 6/2006 | Korlach et al. |
| 7,064,197 | B1 | 6/2006 | Rabbani et al. |
| 7,405,281 | B2 * | 7/2008 | Xu et al. ............ 536/4.1 |

(Continued)

FOREIGN PATENT DOCUMENTS

EP 1105529 B1 11/2005

(Continued)

OTHER PUBLICATIONS

Tarusova et al. Bioorganicheskaya Khimiya, (1985) vol. 11, No. 6, pp. 802-807 (abstract only).*
M. J. Levene, et al., "Zero-Mode Waveguides for Single-Molecule Analysis at High Concentrations," *Science*, 299:682-686 (Jan. 31, 2003).

*Primary Examiner*—Jezia Riley
(74) *Attorney, Agent, or Firm*—Matthew B. Murphy

(57) ABSTRACT

Labeled nucleotide analogs used in place of naturally occurring nucleoside triphosphates or other analogs in template directed nucleic acid synthesis reactions and other nucleic acid reactions, and various analyses based thereon, including DNA sequencing, single base identification, hybridization assays and others.

9 Claims, 9 Drawing Sheets

U.S. PATENT DOCUMENTS

| | | |
|---|---|---|
| 2003/0077610 A1 | 4/2003 | Nelson et al. |
| 2003/0124576 A1 | 7/2003 | Kumar et al. |
| 2003/0162213 A1 | 8/2003 | Fuller et al. |
| 2003/0186276 A1 | 10/2003 | Odera |
| 2003/0190647 A1 | 10/2003 | Odera |
| 2003/0194740 A1 | 10/2003 | Williams |
| 2003/0215862 A1 | 11/2003 | Parce et al. |
| 2004/0048300 A1 | 3/2004 | Sood et al. |
| 2004/0048301 A1 | 3/2004 | Sood et al. |
| 2004/0152119 A1 | 8/2004 | Sood et al. |
| 2004/0214199 A1 | 10/2004 | Schwartz et al. |
| 2004/0224319 A1 | 11/2004 | Sood et al. |
| 2004/0241716 A1 | 12/2004 | Kumar et al. |
| 2005/0032081 A1 | 2/2005 | Ju et al. |
| 2005/0069912 A1 | 3/2005 | Lee et al. |

FOREIGN PATENT DOCUMENTS

| | | |
|---|---|---|
| WO | WO 91/06678 | 5/1991 |
| WO | WO 96/27025 | 9/1996 |
| WO | WO 99/05315 | 2/1999 |
| WO | WO 00/36152 | 6/2000 |
| WO | WO 01/16375 A2 | 3/2001 |
| WO | WO 02/29003 A2 | 4/2002 |

\* cited by examiner

LABELED NUCLEOTIDE ANALOGS AND USES THEREFOR

CROSS-REFERENCE TO RELATED APPLICATIONS

This application is a continuation U.S. patent application Ser. No. 11/241,809 filed Sep. 29, 2005, the full disclosure of which is incorporated herein in its entirety for all purposes.

STATEMENT REGARDING FEDERALLY SPONSORED RESEARCH

Not Applicable.

BACKGROUND OF THE INVENTION

In nucleic acid analyses and nucleic acid based therapies, the use of compositions that are similar in structure to naturally occurring nucleotides or their polymers are widely used. For example, in conventional Sanger type nucleic acid sequencing operations, dideoxynucleotides are employed during template directed synthesis, to provide a synthesis termination event associated with a given type of nucleotide. By identifying the relative length of differentially terminated fragments, one can, by comparison to other, shorter and longer synthesized strands, determine the identity and position of the complementary nucleotide in the template sequence. Variations on the Sanger methods include the use of differentially labeled terminators, such that the various fragments in a mixture have a length component to define the relative position of the terminator, as well as a color component to identify at which base synthesis was terminated (See, e.g., U.S. Pat. Nos. 5,821,058 and 5,171,534).

Likewise, nucleotides or polynucleotide probes labeled with complementary members of fluorescent resonant energy transfer dyes, or FRET pairs, are used widely in performing analysis of polymerase chain reactions, in real time (RT-PCR), and in Sanger related sequencing methods. (See U.S. Pat. Nos. 5,688,648, and 6,150,107).

Though a variety of different molecules have been developed that mimic nucleotides and their polymers in a number of different situations, a number of other applications would be opened to such molecules having new and different properties, such as their ability to be recognized and acted upon by enzymes that process such nucleic acids, their stability in reaction mixtures, and the like. The present invention meets these and a variety of other needs.

SUMMARY OF THE INVENTION

The present invention is generally directed to compositions that comprise compounds that are analogous to nucleotides, and which, in preferred aspects are readily processible by nucleic acid processing enzymes, such as polymerases. The compounds of the invention generally benefit from one or more advantages of greater stability to undesired enzymatic or other cleavage or non-specific degradation, as well as incorporation efficiencies that are better than or at least comparable to triphosphate, tetraphosphate or pentaphosphate analogs.

In at least one aspect, the present invention provides a composition comprising a compound of the formula:

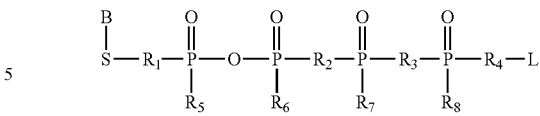

wherein B is a nucleobase; S is selected from a sugar moiety, an acyclic moiety or a carbocyclic moiety; L is a detectable label; $R_1$ is selected from O and S; $R_2$, $R_3$ and $R_4$ are independently selected from O, NH, S, methylene, substituted methylene, C(O), C(CH$_2$), CNH$_2$, CH$_2$CH$_2$, C(OH)CH$_2$R where R is 4-pyridine or 1-imidazole, provided that $R_4$ may additionally be selected from

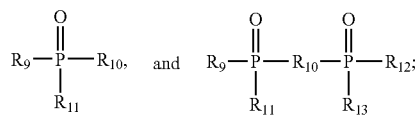

$R_5$, $R_6$, $R_7$, $R_8$, $R_{11}$ and $R_{13}$ are, when present, each independently selected from O, BH$_3$, and S; and $R_9$, $R_{10}$ and $R_{12}$ are independently selected from O, NH, S, methylene, substituted methylene, CNH$_2$, CH$_2$CH$_2$, C(OH)CH$_2$R where R is 4-pyridine or 1-imidazole; provided that if $R_2$ and $R_3$ are O and $R_4$ is O, O—PO$_3$ or O—(PO$_3$)$_2$, then at least one of $R_5$, $R_6$ and $R_7$ is not O.

The present invention also provides methods of using the compounds described herein in performing nucleic acid analyses, and particularly nucleic acid sequence analyses. The methods of the invention typically comprise providing a template nucleic acid complexed with a polymerase enzyme in a template dependent polymerization reaction to produce a nascent nucleic acid strand, contacting the polymerase and template nucleic acid with a compound of the invention, and detecting whether or not the compound was incorporated into the nascent strand during the polymerization reaction, and identifying a base in the template strand based upon incorporation of the compound. Preferably, the foregoing process is carried out so as to permit observation of individual nucleotide incorporation reactions, through the use of, for example, an optical confinement, that allows observation of an individual polymerase enzyme, or through the use of a heterogeneous assay system, where label groups released from incorporated analogs are detected.

DETAILED DESCRIPTION OF THE INVENTION

Figure 1A:
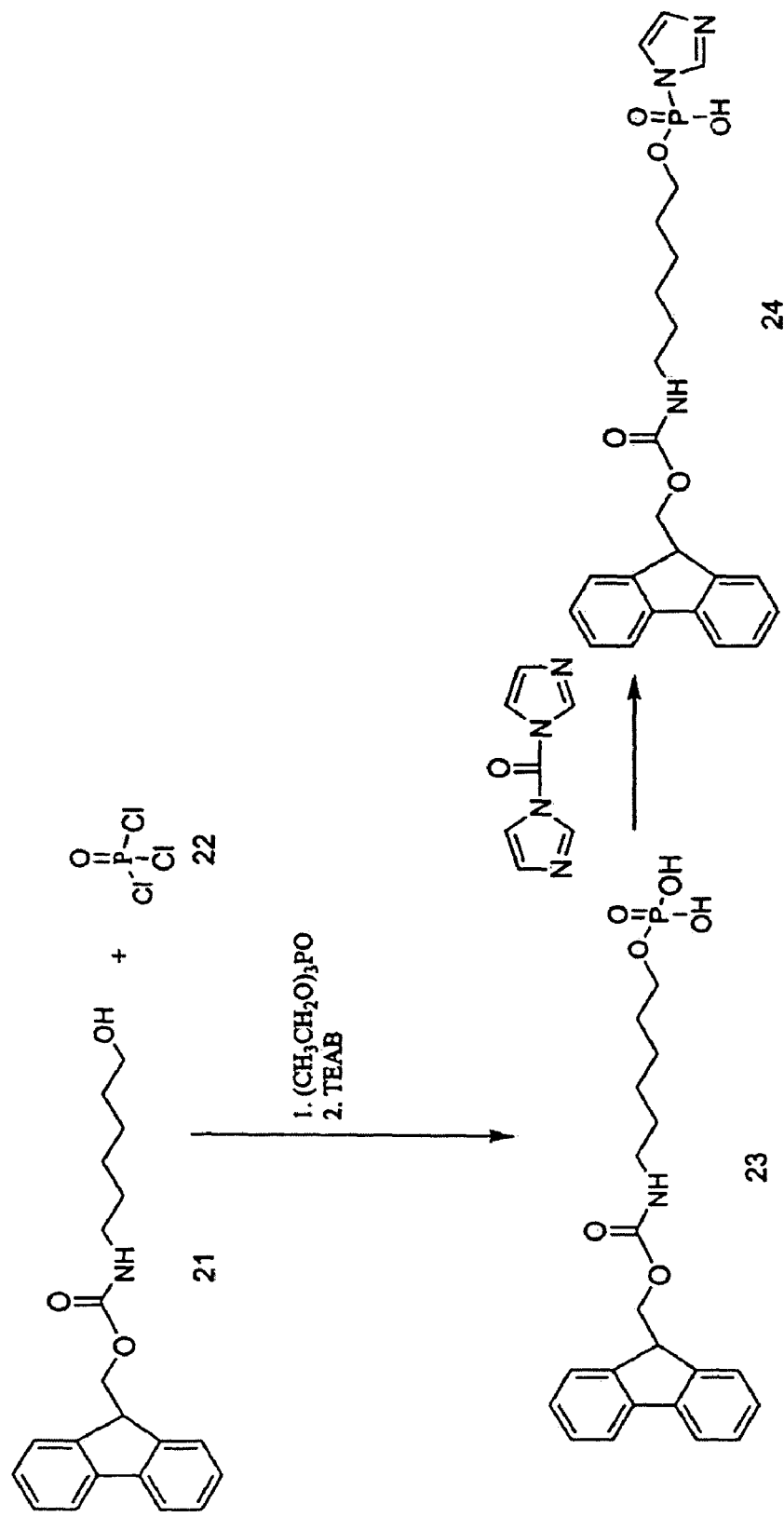
FIG. 1 shows a synthetic scheme for producing an exemplary compound of the invention.

The present invention is generally directed to improved compounds useful as labeled analogs to naturally occurring nucleoside triphosphates or previously described analogs in a variety of different applications, including particularly, analytical nucleic acid analyses such as genotyping, sequencing and other characterization and identification analyses. The compounds of the invention, in addition to providing a detectable label for the monitoring of a given reaction, also provide greater processibility by nucleic acid processing enzymes, i.e., polymerases, relative to labeled nucleoside triphosphates, and greater stability relative to other labeled nucleotide analogs, e.g., nucleoside tetra and pentaphosphates (See, e.g., Published U.S. Patent Application No. 2003/0124576).

I. Compounds

Generally speaking, the compounds of the invention provide a nucleoside moiety or an analog thereof, to which is coupled a phosphorus containing chain, containing from 4 to 6 phosphorus atoms, linked to a nucleoside moiety, where such phosphorus atoms are optionally substituted at various side positions, and optionally linked at one or more positions by other than an oxygen atom. Without being bound to any particular theory of operation, it is believed that improved incorporation efficiencies, of the compounds of the invention, or processability by the polymerase enzyme, are obtained by providing a labeling moiety a greater distance from the nucleoside (or nucleoside-like) moiety, and or by providing selective substitution of side groups and/or the constituents of the main chain, proximal to the nucleoside moiety. Greater stability of the compounds of the invention is believed to result from the inclusion of more stable linkages joining phosphorus containing groups away from what would be the alpha phosphate of a naturally occurring nucleotide, e.g., at the linkage corresponding to the β-γ phosphate linkage of a nucleoside triphosphate or γ-δ linkage of a nucleoside tetraphosphate, as well as by, again, selectively substituting side groups within the phosphorus containing chain.

In describing the compounds and compositions of the invention in terms of being analogs to nucleotides, is meant that in a particular application, the compounds or compositions function in a manner similar to or analogous to naturally occurring nucleoside triphosphates (or nucleotides), and does not otherwise denote any particular structure to such compounds. In particular, the compounds of the invention are particularly useful as substrates for polymerase enzymes in polynucleotide synthesis and particularly, template dependent polynucleotide synthesis, e.g., DNA polymerases, i.e., Taq polymerases, E. coli DNA Polymerase 1, Klenow fragment, reverse transcriptases, Φ29 related polymerases including wild type Φ29 polymerase and derivatives of such polymerases, T7 DNA Polymerase, T5 DNA Polymerase, RNA polymerases, and the like, where such synthesis is a component of a process for the identification of sequence elements in the polynucleotide, e.g., individual bases, contiguous sequences of nucleotides, and/or overall nucleic acid composition, and the like.

One advantage of many of the compounds of the invention is their ability to be recognized and processed by nucleic acid processing enzymes, and particularly polymerase enzymes. In particular, the compounds of the invention are generally able to be incorporated by polymerase enzymes into growing polynucleotide strands, and are more particularly incorporated into the growing strand in a template dependent synthesis. Another particular advantage of the compounds of the invention is that while they include a label moiety as individual molecules, in order for the analogs to be processed and incorporated into a synthesized nucleic acid strand, the label group is cleaved from the analog by the action of the polymerase, and thus the label is not incorporated into the synthesized strand.

The removal of the label group provides a number of benefits, including for example, the avoidance of any steric interference on a subsequent incorporation event, from bulky or chemically incompatible label groups, that could effectively terminate or reduce the rate of continued synthesis, and the ability to detect the incorporation event by allowing differential labeling, and therefore detection, of substrate (labeled analog monomers) and product (unlabeled polymer).

Another advantage of the compounds of the invention relative to conventional labeled nucleoside polyphosphates, is the incorporation of substituents that improve the stability of the analogs and/or improve the efficiency of their incorporation by nucleic acid polymerases, as well as improve the stability of nucleic acids synthesized using such analogs to exonucleoases. In particular, by coupling phosphonate groups to the underlying nucleoside or nucleoside analog, one may impart additional stability of the labeled monomers in solution. In particular, while phosphatases, pyrophosphatases, and phosphodiesterases may undesirably cleave phosphate groups and associated label groups from labeled nucleoside polyphosphate analogs, the inclusion of non-ester linkages should prevent any such cleavage.

The compounds of the invention are generally represented by the formula:

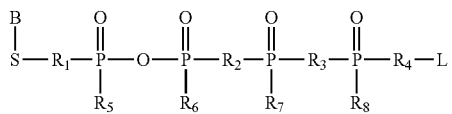

In the above illustrated structure, B represents a natural or non-natural nucleobase or nucleobase analog. S is selected from a sugar moiety, an acyclic moiety or a carbocyclic moiety. L is a detectable label optionally including a linker. $R_1$ is selected from O and S. $R_2$, $R_3$ and $R_4$ are typically independently selected from O, methylene, substituted methylene, ethylene, substituted ethylene, where the substitutents may include H, F, Cl, OH, $NH_2$, alkyl, alkenyl, alkynyl, aryl, and heterocycle. In structural terms, the carbons of the substituted methylene or ethylene groups will generally comprise the structure CR'R", where R' and R" are independently selected from H, F, Cl, OH, $NH_2$, alkyl, alkenyl, alkynyl, aryl, and heterocycle. Examples of such groups include, e.g., $CH_2$, $CF_2$, $CCl_2$, $C(OH)(CH_3)$, $C(NH_2)[(CH_2)_6CH_3])$ and $CH_2CH_2$. $R_2$, $R_3$ and $R_4$ are also selected from NH, S, CH(NHR) (where R is H, alkyl, alkenyl, alkynyl. aryl, or heterocycle), $C(OH)[(CH_2)_nNH2]$ (n is 2 or 3), $C(OH)CH_2R$ where R is 4-pyridine or 1-imidazole. and $CNH_2$.

In preferred aspects, $R_2$, $R_3$ and in some cases $R_4$, are independently selected from O, NH, S, methylene, substituted methylene, $CNH_2$, $CH_2CH_2$, $C(OH)CH_2R$ where R is 4-pyridine or 1-imidazole.

In addition to the foregoing, $R_4$ is additionally selected from selected from

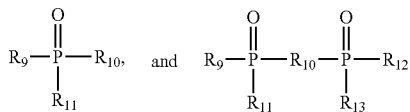

$R_5$, $R_6$, $R_7$, $R_8$, $R_{11}$ and $R_{13}$ are, when present, each independently selected from O, $BH_3$, and S; and $R_9$, $R_{10}$ and $R_{12}$ are typically independently selected from the same groups as $R_2$ and $R_3$. In the case where both $R_2$ and $R_3$ are O and $R_4$ is O, O—$PO_3$ or O—$(PO_3)_2$, then at least one of $R_5$, $R_6$ and $R_7$ is not O.

The base moiety incorporated into the compounds of the invention is generally selected from any of the natural or non-natural nucleobases or nucleobase analogs, including, e.g., purine or pyrimidine bases that are routinely found in nucleic acids and nucleic acid analogs, including adenine, thymine, guanine, cytidine, uracil, and in some cases, inosine. For purposes of the present description, nucleotides and nucleotide analogs are generally referred to based upon their relative analogy to naturally occurring nucleotides. As such, an analog that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention may include the conventional bases described herein or they may include such bases substituted at one or more side groups, or other fluorescent bases or base analogs, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

In the compounds of the invention, the S group is preferably a sugar moiety that provides a suitable backbone for a synthesizing nucleic acid strand. In it most preferred aspect, the sugar moiety is selected from a D-ribosyl, 2' or 3' D-deoxyribosyl, 2',3'-D-dideoxyribosyl, 2',3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties may be incorporated as the "S" group in place of a sugar moiety, including, e.g., those described in published U.S. Patent Application No. 2003/0124576, previously incorporated herein by reference in its entirety for all purposes.

For most cases, the phosphorus containing chain in the compounds of the present invention, e.g., a triphosphate in conventional NTPs, is preferably coupled to the 5' hydroxyl group, as in natural nucleoside triphosphates. However, in some cases, it may be desirable that the phosphorus containing chain is linked to the S group by the 3' hydroxyl group.

As used herein and as noted above, L generally refers to a detectable labeling group that is coupled to the terminal phosphorus atom via the $R_4$ (or $R_{10}$ or $R_{12}$) group. The labeling groups employed in the analogs of the invention may comprise any of a variety of detectable labels. Detectable labels generally denote a chemical moiety that provides a basis for detection of the analog compound separate and apart from the same compound lacking such a labeling group. Examples of labels include, e.g., optical labels, e.g., labels that impart a detectable optical property to the analog, electrochemical labels, e.g., labels that impart a detectable electrical or electrochemical property to the analog, physical labels, e.g., labels that impart a different physical or spatial property to the analog, e.g., a mass tag or molecular volume tag. In some cases individual labels or combinations may be used that impart more than one of the aforementioned properties to the analogs of the invention.

In preferred aspects, the labeling groups incorporated into the analogs of the invention comprise optically detectable moieties, including luminescent, chemiluminescent, fluorescent, fluorogenic, chromophoric and/or chromogenic moieties, with fluorescent and/or fluorogenic labels being particularly preferred. A variety of different label moieties are readily employed in nucleotide analogs, and particularly, the compound of the invention. Such groups include fluorescein labels, rhodamine labels, cyanine labels (i.e., Cy3, Cy5, and the like, generally available from the Amersham Biosciences division of GE Healthcare), the Alexa family of fluorescent dyes and other fluorescent and fluorogenic dyes available from Molecular Probes/Invitrogen, Inc., and described in 'The Handbook—A Guide to Fluorescent Probes and Labeling Technologies, Tenth Edition' (2005) (available from Invitrogen, Inc./Molecular Probes). A variety of other fluorescent and fluorogenic labels for use with nucleoside polyphosphates, and which would be applicable to the compounds of the present invention are described in, e.g., Published U.S. Patent Application No. 2003/0124576, the full disclosure of which is incorporated herein in its entirety for all purposes.

For a number of applications, it may be desirable to utilize a different type of labeling group for each analog that includes a different base, e.g., A, T, G, C (as well as U or I). In such cases, the fluorescent or fluorogenic labels may be selected so that each label absorbs excitation radiation and/or emits fluorescence, at a distinguishable wavelength from the other label groups. Such distinguishable analogs provide an ability to monitor the presence of different labels simultaneously in the same reaction mixture.

In the case of applications where multiple different labels are used in the different analogs, fluorescent label groups may be selected to include overlapping excitation spectra, so as to avoid the necessity for multiple different excitation sources, while providing clearly distinguishable emission spectra.

While different individual fluorescent dye groups may be used that have at least partially overlapping excitation spectra, in some cases, it may be desirable to employ multicomponent fluorescent labels on different analogs. For example, fluorescent resonant energy transfer ("FRET") labels may be used as the label group. FRET labels typically include a donor group (donor fluorophore) and an acceptor group (acceptor fluorophore) where, in response to a given excitation radiation, the excited donor transfers all or part of the absorbed energy to the acceptor fluorophore, rather than emitting fluorescence itself. The acceptor then emits fluorescence in returning to its relaxed state. The use of such FRET pairs allows for a greater degree of selectability of the excitation and emission spectra for the compounds of the invention. In particular, across a variety of different analogs, one can utilize a single type donor fluorophore that has a single excitation spectrum, but couple it with four different acceptor fluorophores (e.g., having an excitation spectrum that at least partially overlaps with the emission spectrum of the donor), where each different acceptor fluorophore has a different emission spectrum. The configuration of a variety of different analogs having the same or similar excitation spectra and multiple different emission spectra has broad utility in a variety of multiplexed analyses, including for example, four color nucleic acid sequencing applications. In particular, the use of a single excitation light source dramatically reduces engineering constraints for excitation/detection systems, and also provides a more uniform analog structure to potentially provide more predictability and/or uniformity for any biochemistry steps involve in the processes, i.e., except for differences in the base and the acceptor fluorophore.

In alternative aspects, FRET pairs may be employed that result in generation of a fluorescent signal when the analog is processed, e.g., incorporated into a nucleic acid strand by a polymerase. In particular, the donor and acceptor fluorophores may be coupled to different portions of the analog, e.g., having a donor present on a base, sugar or alpha phosphate group, while the acceptor is coupled to a distal phosphorus group, e.g., the terminal phosphorus group, but such that the distance between the donor and acceptor is sufficient to provide quenching of fluorescence from the donor. Upon cleavage of the linkage between the $\alpha$ and $\beta$ phosphorus atoms during polymerase driven polymerization, the acceptor is released from the analog, un-quenching the donor and producing a fluorescent signal in response to excitation radiation.

Examples of useful FRET label pairs include, e.g., those described in U.S. Pat. Nos. 5,654,419, 5,688,648, 5,853,992, 5,863,727, 5,945,526, 6,008,373, 6,150,107, 6,335,440, 6,348,596, 6,479,303, 6,545,164, 6,849,745 and 6,696,255, and Published U.S. Patent Application No. 2003/0143594, the disclosures of which are incorporated herein by reference for all purposes.

As noted previously, other labeling groups may optionally be incorporated into the compounds of the invention. Such labels include mass based labels, e.g., molecular tags of differing molecular weights, that allow differential size based separation of the compounds, or their reaction products. Likewise, such labels may include electrochemical labels, where the labeling moiety imparts a differential charge on different compounds, thus facilitating its detection either by virtue of its differential electrophoretic mobility or by detecting a field effect or electrochemical change from the localized charge, e.g., using a ChemFET, conductivity sensors, or the like. Examples of such electrochemical labels include, e.g., e-Tags™ marketed by Monogram Biosciences, Inc. of Mountain View, Calif. Other label groups useful in the present invention include those which yield a colored product, e.g., p-nitrophenyl derivatives, or a product that is luminescent or that can be translated into a luminescent signal, e.g., through an included enzymatic cascade.

As noted previously, the elongated phosphorus containing chain, e.g., containing four or more phosphorus atoms in a linear configuration, is believed to provide an advantage in the presently described compounds by placing labeling molecules that may be foreign to nucleotide processing enzymes, e.g., DNA polymerases, away from the relevant portion of the analog and/or away from the active site of the enzyme. In addition to providing such distance through the phosphorus containing chain, additional linker molecules may be used to provide additional distance between the nucleoside portion of the analog, and the label group. In particular, while the label group may be directly coupled to the terminal phosphorus atom of the analog structure, in alternative aspects, it may additionally include a linker molecule to provide the coupling through, e.g., an alkylphosphonate linkage.

A wide variety of linkers and linker chemistries are known in the art of synthetic chemistry may be employed in coupling the labeling group to the analogs of the invention. For example, such linkers may include organic linkers such as alkane or alkene linkers of from about C2 to about C20, or longer, polyethyleneglycol (PEG) linkers, aryl, heterocyclic, saturated or unsaturated aliphatic structures comprised of single or connected rings, amino acid linkers, peptide linkers, nucleic acid linkers, PNA, LNAs, or the like or phosphate or phosphonate group containing linkers. In preferred aspects, alkyl, e.g., alkane, alkene, alkyne alkoxy or alkenyl, or ethylene glycol linkers are used. Some examples of linkers are described in Published U.S. Patent Application No. 2004/0241716, which is incorporated herein by reference in its entirety for all purposes. Additionally, such linkers may be selectively cleavable linkers, e.g., photo- or chemically cleavable linkers or the like.

As noted previously, the compounds of the invention typically differ from polyphosphates by virtue of the inclusion of one or more phosphonate groups, effectively substituting a non-ester linkage in the phosphorous containing chain of the analog, with a more stable linkage. Examples of preferred linkages include, e.g., $CH_2$, methylene derivatives (e.g., substituted independently at one or more hydrogens with F, Cl, OH, NH2, alkyl, alkenyl, alkynyl, etc.), $CCl_2$, $CF_2$, NH, S, $CH_2CH_2$, $C(OH)(CH_3)$, $C(NH_2)[(CH_2)_6CH_3]$, $CH(NHR)$ (R is H or alkyl, alkenyl, alkynyl, aryl, $C(OH)[(CH_2)_nNH2]$ (n is 2 or 3), and $CNH_2$. In particularly preferred aspects, methylene, amide or their derivatives are used as the linkages.

In preferred aspects, the compounds include one, two or three of such linkages, but retain an alpha phosphate that is coupled to the sugar (or carbocyclic or acyclic) moiety of the analog. Retention of the alpha phosphate group yields several benefits in the compounds of the invention. In particular, it permits cleavage of the beta and more distal phosphorus groups and the associated label from the analog by a polymerase enzyme during processing by that enzyme. Additionally, once processed, the analog is more closely analogous (and in some embodiments, identical) to a naturally occurring, processed nucleotide, allowing base dependent hybridization and further minimizing any steric or other enzyme related effects of incorporation of a highly heterologous compound into a growing nucleic acid strand.

In addition to substitution at the inter-phosphorus linkages, the compounds of the invention are also optionally substituted at one or more of the side groups of the phosphorus atoms (or alpha phosphate). Typically, substitution at these side groups, and particularly those more distal than the alpha phosphate, will have little negative impact on the incorporation of the analog into a growing nucleic acid strand by a nucleic acid polymerase. In some cases, incorporation of certain groups at such side groups is expected to provide improved efficiency of incorporation or processivity of the polymerase enzymes. In particular, boronation of one or more of the subject side groups is expected to provide such enhanced incorporation. In particularly preferred aspects, the at least one of the oxygen groups on the $\alpha$ phosphate are substituted with Boron, and more preferably, the boronated-$\alpha$-phosphate is the Rp stereo isomer (See, Ramsey-Shaw, et al., Reading, Writing and Modulating Genetic Information with Boranophosphate Mimics of Nucleotides, DNA, and RNA, (2003) Ann. N.Y. Acad. Sci. 1002:12-29, which is incorporated herein by reference in its entirety for all purposes). Such $\alpha$-P-Borane substitutions have been shown to improve substrate characteristics for nucleotide analogs, i.e., AZT triphosphate, d4T triphosphate, and 3TCTP in reactions with HIV-1 RT (See, Phillippe Meyer et al., EMBO J. (2000) 19:3520-3529, and Jerome Deval, et al., J. Biol. Chem. (2005) 280:3838-3846). Additionally, borane modified nucleic acids have been shown to be resistant to exonucleoase activity (See Ramsey-Shaw et al. supra.). In accordance with certain preferred uses of the compounds of the invention, increased stability of a nascent nucleic acid strand to exonuclease activity can be of substantial value, in preventing auto-corrections for misincorporation of a nucleotide during the synthesis process. Such corrections can yield substantial data analysis problems in processes that utilize real time observation of incorporation events as a method of identifying sequence information.

While the compounds of the invention are generally described in terms of including four or more phosphorus groups in the phosphorus containing chain, it will be appreciated that in some instances a three phosphorus atom containing chain may be desired. In such cases, the group $R_3$—P(O)—$R_8$ would not be included in the structure, and would be replaced by the $R_4$ group and its variations.

Examples of certain preferred compounds of the invention include those shown below:

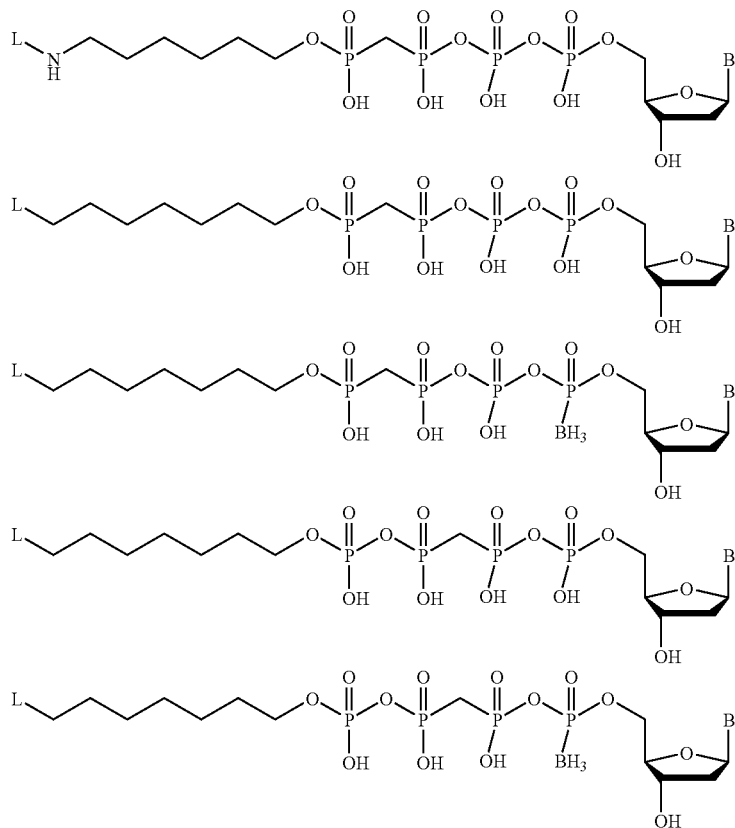

Although shown for purposes of illustration, it will be appreciated that the compounds of the invention encompass a range of variability, including, in particularly preferred aspects, that which is set forth in the appended claims.

II. Applications of Compounds

The compounds and compositions of the invention have a variety of different uses and applications. In particular, the labeled compounds of the invention are particularly useful in performing nucleic acid analyses. For example, such compounds may be used as signaling analogs to indicate incorporation into a growing nucleic acid strand. Such signaling may be the result of detecting labeling groups that are liberated from the incorporated analog, e.g., in a solid phase assay, or it may arise upon the incorporation reaction. For example, in the case of FRET labels where the bound label is quenched and the free label is not, the release of the label group from the incorporated analog can give rise to a fluorescent signal.

Alternatively, the reaction of interest, e.g., the polymerase reaction, can be isolated within an extremely small observation volume that effectively results in observation of individual polymerase molecules. As a result, the incorporation event provides observation of an incorporating nucleotide analog that is readily distinguishable from non-incorporated nucleotide analogs. In a preferred aspect, such small observation volumes are provided by immobilizing the polymerase enzyme within an optical confinement, such as a Zero Mode Waveguide. For a description of ZMWs and their application in single molecule analyses, and particularly nucleic acid sequencing, see, e.g., Published U.S. Patent Application No. 2003/0044781, and U.S. Pat. No. 6,917,726, each of which is incorporated herein by reference in its entirety for all purposes.

In accordance with one aspect of the methods of invention, the compounds described herein are used in analyzing nucleic acid sequences using a template dependent polymerization reaction to monitor the template dependent incorporation of specific analogs into a synthesized nucleic acid strand, and thus determine the sequence of nucleotides present in the template nucleic acid strand. In particular, a polymerase enzyme is complexed with the template strand in the presence of one or more nucleotides and/or one or more nucleotide analogs of the invention. In preferred aspects, only the labeled analogs of the invention are present representing analogous compounds to each of the four natural nucleotides, A, T, G and C. When a particular base in the template strand is encountered by the polymerase during the polymerization reaction, it complex with an available analog that is complementary to such nucleotide, and incorporate that analog into the nascent and growing nucleic acid strand, cleaving between the α and β phosphorus atoms in the analog, and consequently releasing the labeling group (or a portion thereof). The incorporation event is detected, either by virtue of a longer presence of the analog in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits a real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a zero mode waveguide.

In addition to their use in sequencing, the analogs of the invention are also equally useful in a variety of other genotyping analyses, e.g., SNP genotyping use single base extension methods, real time monitoring of amplification, e.g., RT-PCR methods, and the like.

III. Kits

The present invention also provides kits useful for exploiting the compounds described herein in a number of applications. In a first respect, such kits typically include the analog of the invention packaged in a fashion to enable their use, and preferably a set of at least four different analogs of the invention, namely those that are analogous to A, T, G, and C, where each bears a detectably different labeling group to permit its individual identification in the presence of the others. Depending upon the desired application, the kits of the invention optionally include additional reagents, such as enzymes, like polymerase enzymes, for performing template dependent synthesis employing the analogs of the invention, a control sequence, and other reagents, such as buffer solutions and/or salt solutions, including, e.g., divalent metal ions, i.e., $Mg^{++}$, $Mn^{++}$ and/or $Fe^{++}$, standard solutions, e.g., dye standards for detector calibration. Such kits also typically include instructions for use of the compounds and other reagents in accordance with the desired application methods, e.g., nucleic acid sequencing, and the like.

IV. Synthesis of Compounds

The compounds of the invention are generally synthesizable using methods known to those of ordinary skill in the art. In particular, substituted diphosphoro, triphosphoro or tetraphosphoro compounds may generally be coupled with nucleoside mono, di or triphosphates to position alternative linkages between the α-β, β-γ, γ-δ, etc., phosphorus atoms in the chain.

By way of example, such a synthesis strategy may be used in producing a methylene phosphonate dye labeled nucleotide analog having the structure:

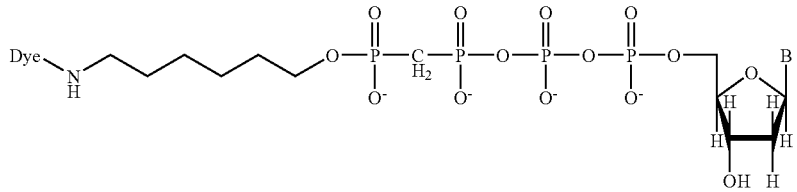

In particular, methylenebisphosphorochloride, or any of a variety of other bisphosphonates, may be used as a starting material that would provide a relatively direct route to the final compound, according to the following synthesis scheme:

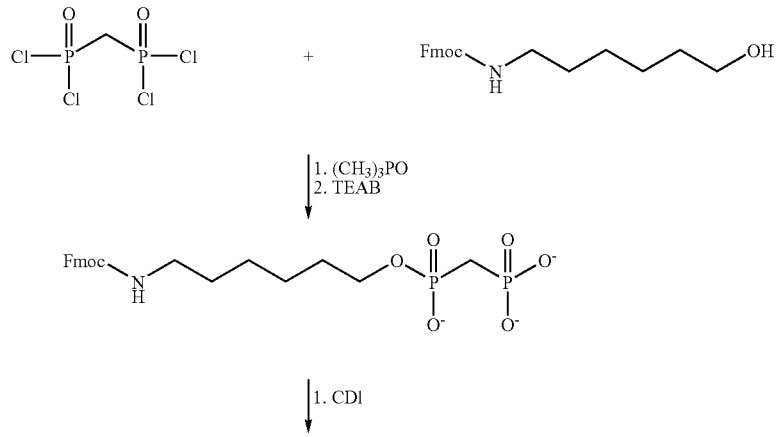

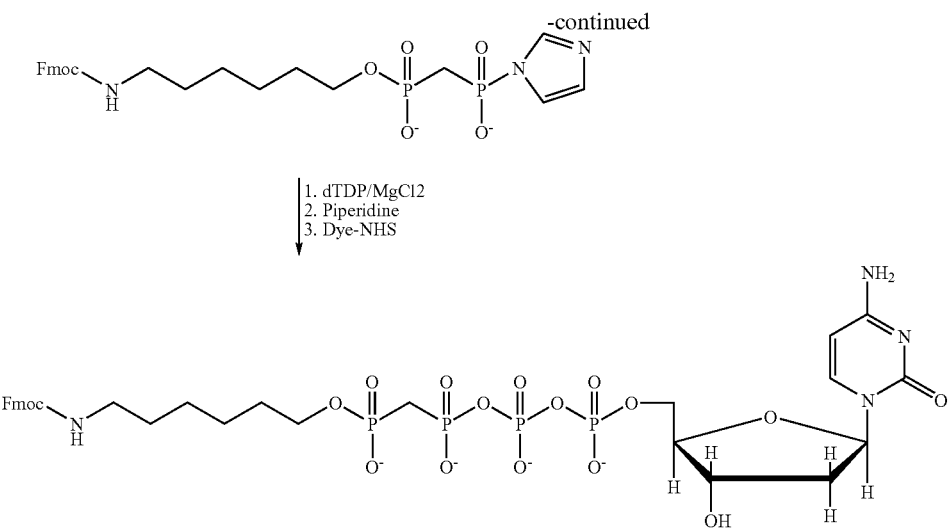

In producing a γ-δ phosphonate, an alternate synthesis scheme employs FMOC-aminohexanol or other protected aminoalcohol, which is reacted with an appropriate activating group, e.g., toluenesulfoylchloride or various triflates, to yield an activated alcohol. The activated alcohol may be reacted with a bis-phosphonate to yield, e.g.:

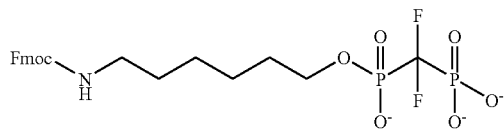

This compound is then reacted with a desired nucleoside diphosphate imidazolate to give the γ-δ phosphonate linked nucleotide compound.

V. EXAMPLES

A number of compounds of the invention were synthesized and tested to determine their efficacy, and these are set forth in the following non-limiting examples.

Example 1

Synthesis of Analog Compounds

Dye NHS esters were purchased from Invitrogen. All other reagents were purchased from Sigma Aldrich unless indicated otherwise. All reported compounds were characterized by HPLC, UV-Vis, fluorescence, $^1$H NMR, and MS where appropriate. Preparative anion exchange high-performance chromatography (AE-HPLC) was performed as follows. Column: HiPrep™ 16/10 Q FF, Sepharose based strong anion exchanger, 16×100 mm (GE Healthcare Amersham Biosciences). Solvent A: 0.05 M triethylammonium bicarbonate (TEAB), pH 8. Solvent B: 1.0 M TEAB, pH 8. Preparative reversed phase high-performance chromatography (RP-HPLC) was performed as follows. Column: Xterra Prep RP18, 5 μm, 19×100 mm (Waters Inc). Solvent A: 0.1 M TEAB, pH 8. Solvent B: acetonitrile. Analytical reversed phase high-performance chromatography (HPLC) was performed as follows. Column: Xterra RP18 5 μm 4.6×150 mm (Waters Inc). Solvent A: 0.1 M triethylammonium acetate (TEAA). Solvent B: acetonitrile. HPLC was employed to monitor the progress of all reactions.

1. Methylene Phosphonate 1

A methylene phosphonate nucleotide analog (A546 Phosphonate β-γ Methylene nucleotide) was synthesized incorporating the methylene linkage between the β and γ phosphorus groups, and having the following formula:

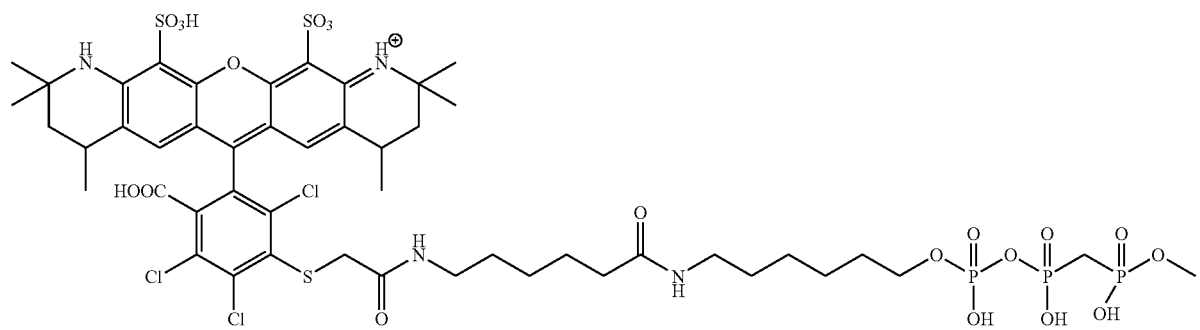

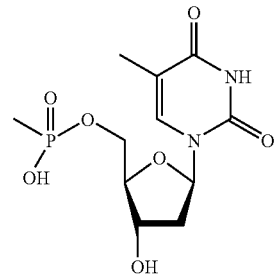

Figure 1B:
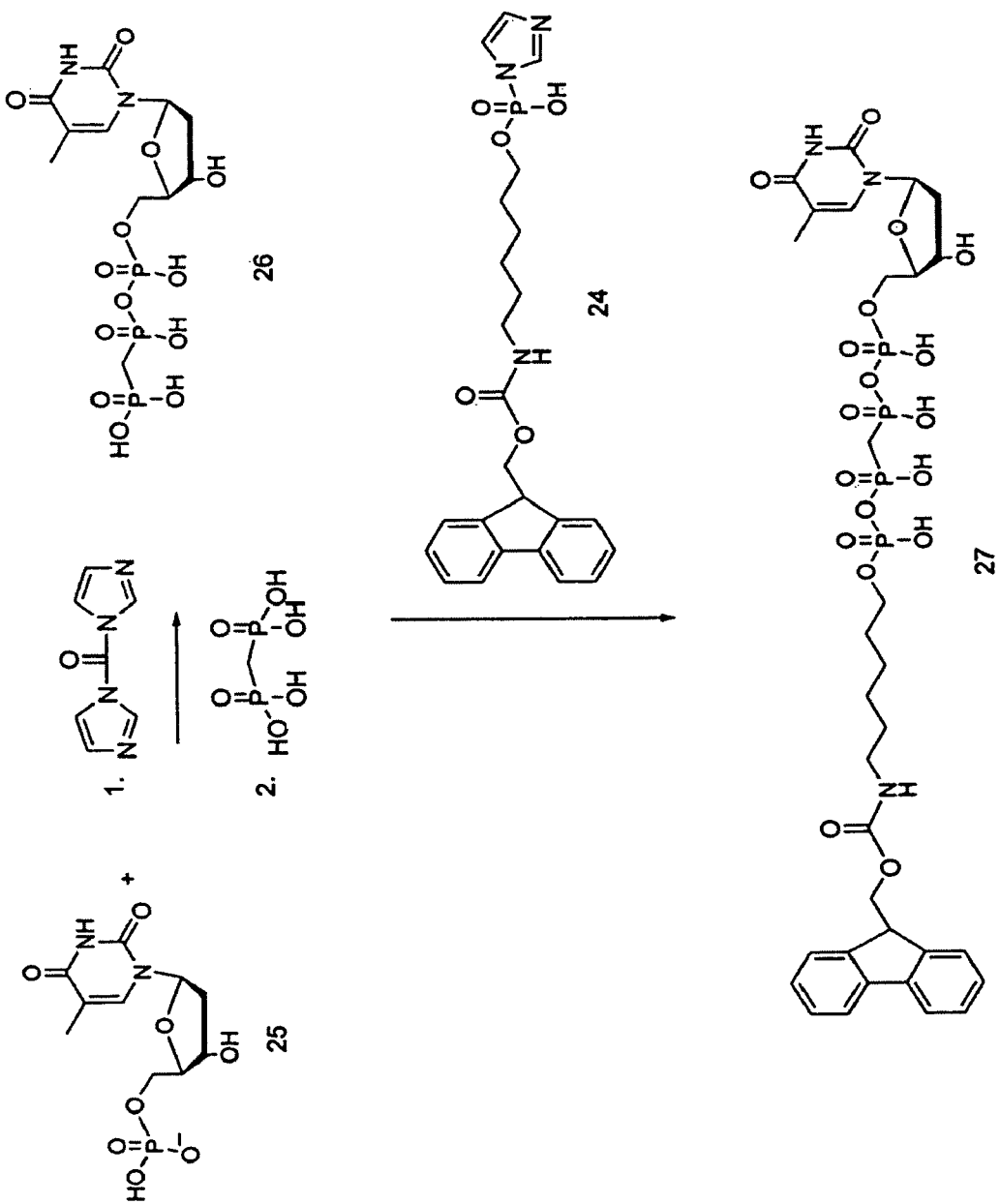
Figure 1C:
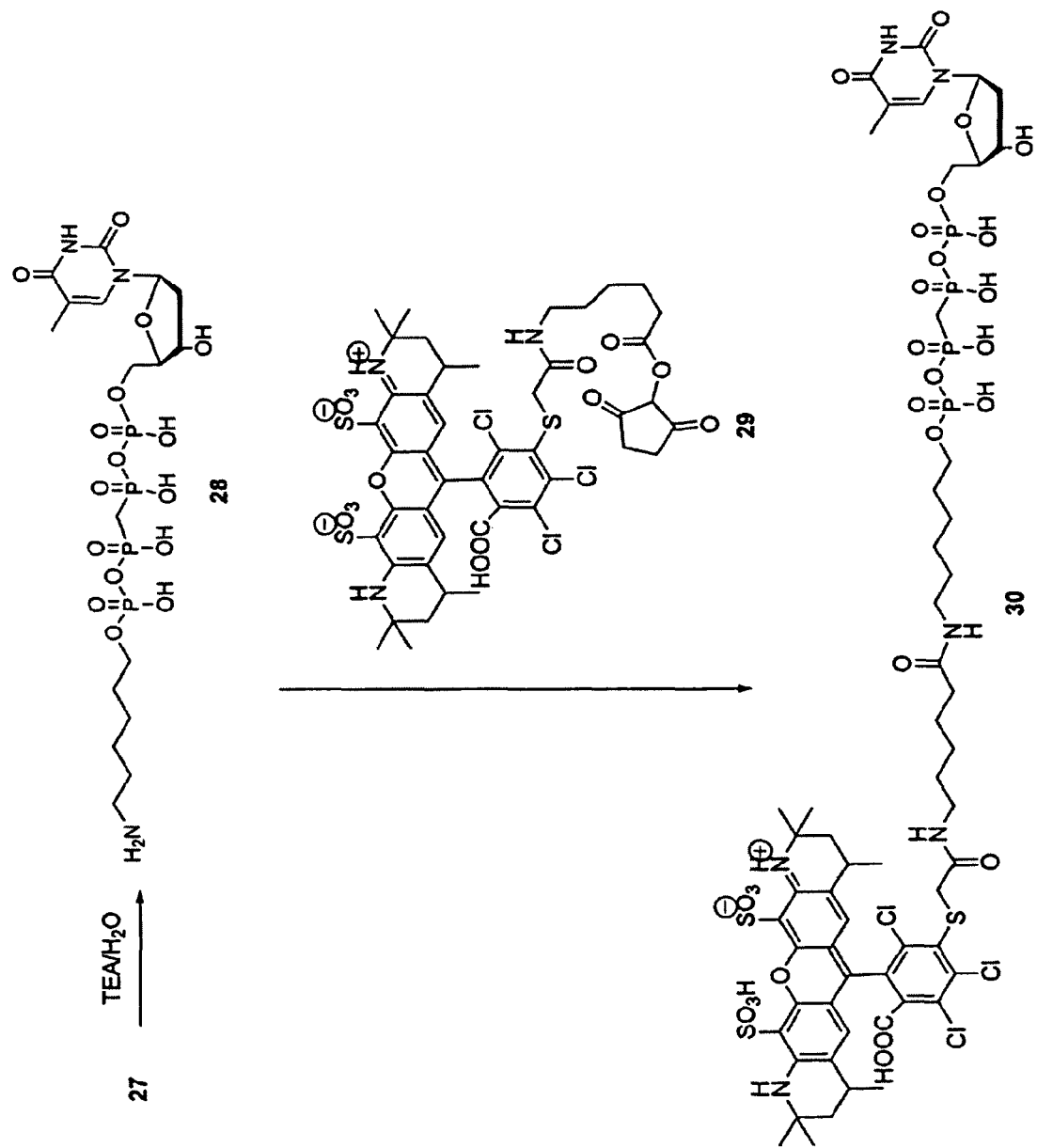

The synthetic scheme for the compound is illustrated in FIGS. 1A, 1B and 1C. To a stirred solution of phosphorus oxychloride 22 (1.5 mMoles) in triethylphosphate (2 ml) was added 170 mg (0.5 mMole) 6-(FMOCamino)1-hexanol 21. The solution was initially cooled in an ice/water bath and warmed to ambient temperature overnight. The reaction was quenched by addition of 5 ml 0.1M triethylamine bicarbonate pH 7. Triethylamine was used to maintain pH 7. The product 23 was isolated by RP-HPLC in TEAB/acetonitrile, followed by coevaporation with methanol. Yield 0.22 mMoles 6-(FMOCamino)hexanel-phosphate 24 (FIG. 1A).

Thymidine 5'monophosphate TBA salt 25 (0.15 mMoles) was coevaporated with acetonitrile and dissolved in 2 ml DMF. Carbonyldiimidazole (0.6 mMole) was added and the solution was stirred for 4 hours at ambient temperature, followed by the addition of 1 mMole anhydrous methanol and stirred for a further half hour. Anhydrous methylenediphosphonate TBA salt (1.5 mMoles) in 2 ml DMF was added to the TMP-imidazolate and stirred at ambient temperature overnight. The reaction mixture was diluted with water and purified by ion exchange chromatography followed by RP-HPLC. The product 26 was coevaporated with methanol followed by coevaporation with acetonitrile. Yield: 0.06 mMole $PCH_2PPdT$ 26 (FIG. 1B).

6-(FMOCamino)hexanel-phosphate (0.15 mmoles) 24 was coevaporated with acetonitrile and dissolved in 2 ml DMF. Carbonyldiimidazole (0.6 mMole) was added and the solution was stirred for 4 hours at ambient temperature, followed by the addition of 1 mMole anhydrous methanol and stirred for a further half hour. Anhydrous $PCH_2PPdT$ 26 (0.06 mMole) was dissolved in 3 ml DMF and added to the 6-FMOCaminohexyl-1-phosphoimidazolate solution. The reaction was stirred 4 hours at ambient temperature, followed by dilution to 10 ml with acetonitrile to yield 27. Triethylamine (1 ml) was added and stirred overnight. The solvent was evaporated, the residue dissolved in water, and purified by ion exchange chromatography, followed by RP-HPLC. Yield: 0.018 mMoles aminohexyl-$PPCH_2PPdT$ 28 (FIG. 1C).

Aminohexyl-$PPCH_2PPdT$ 28 (1 µMole in 100 µL water) was added to 1 mg Alexa546NHS 29 (Invitrogen), followed by 50 µl 0.3M sodiumcarbonate pH9. The mixture was set aside for 2 hr. The product was purified by ion exchange followed by RP-HPLC. The product was coevaporated with methanol and reconstituted in 10 mM Tris. Yield: 340 nMoles A546-aminohexyl-$PPCH_2PPdT$ 30.

2. Methylene Phosphonate 2

A methylene phosphonate nucleotide analog (A546-phosphonate-thymidine) was synthesized incorporating the methylene linkage between the γ and δ phosphorus groups, and having the following formula:

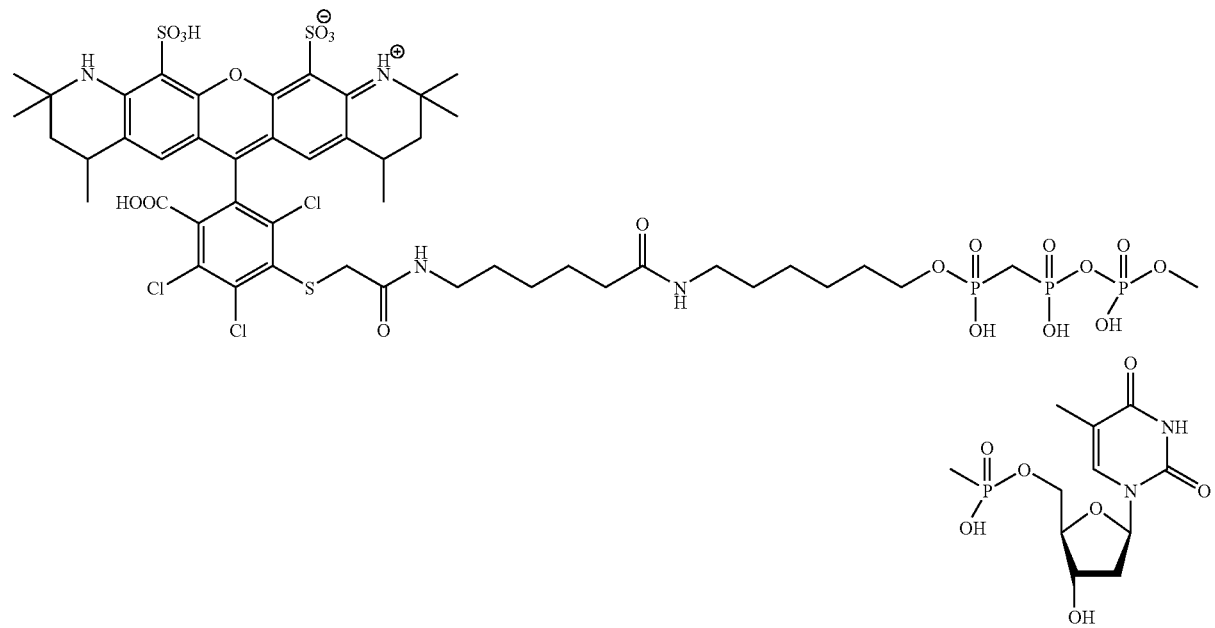

Figure 2A:
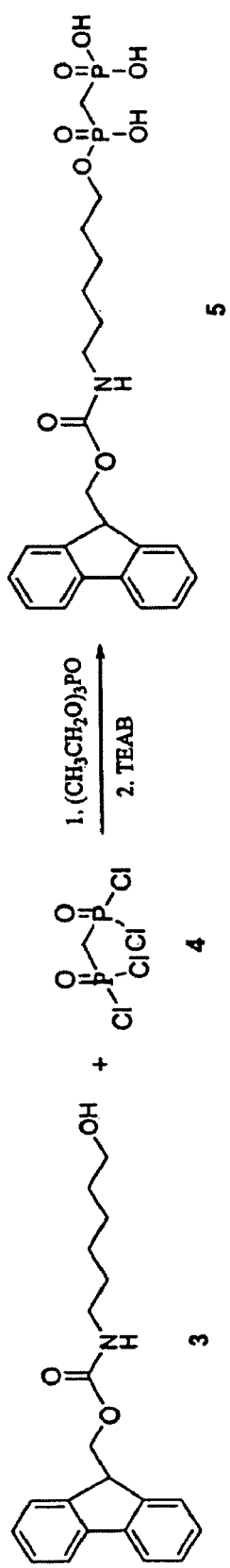
FIGS. 2A, 2B and 2C show synthetic schemes for producing certain exemplary compounds of the invention.
Figure 2B:
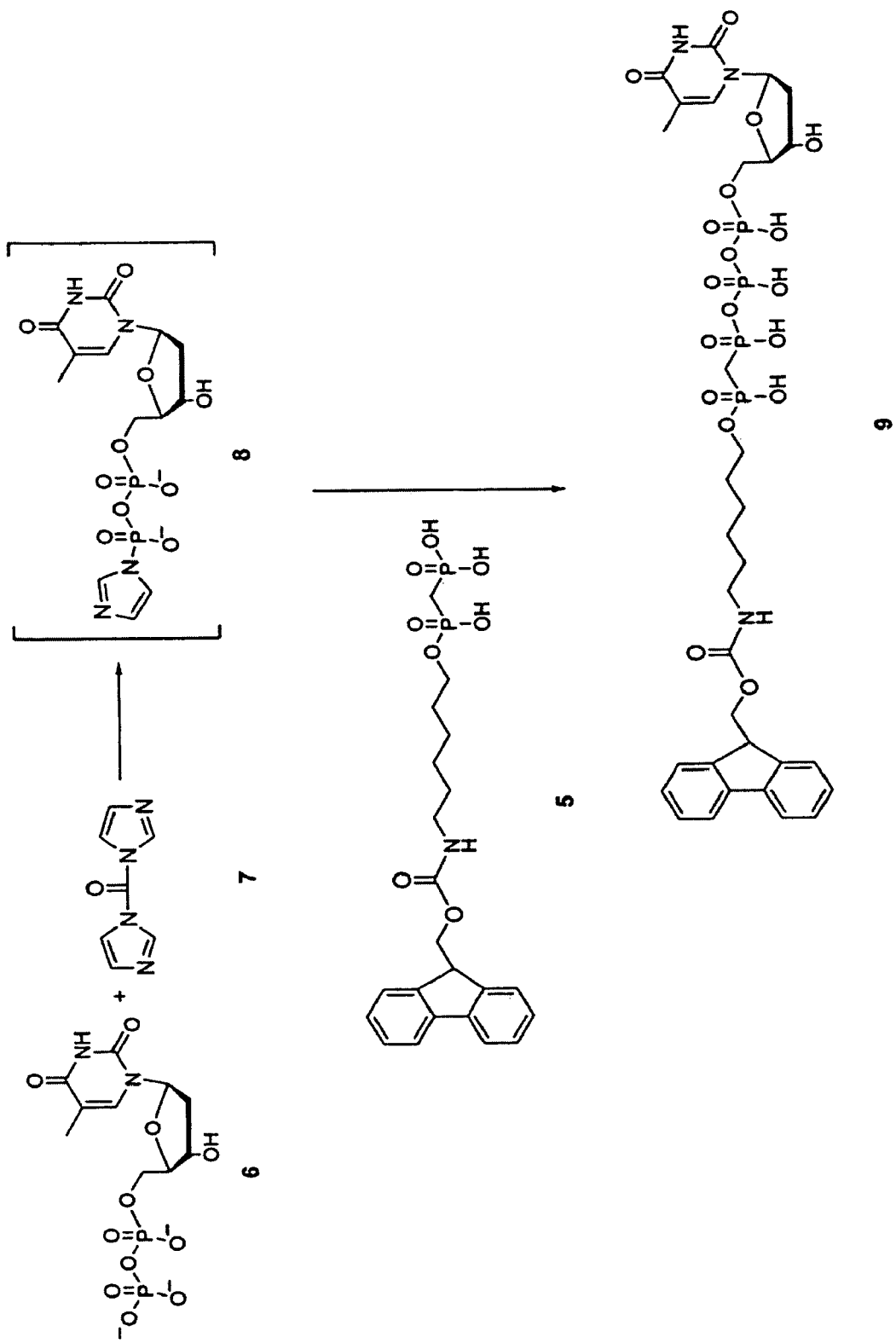
Figure 2C:
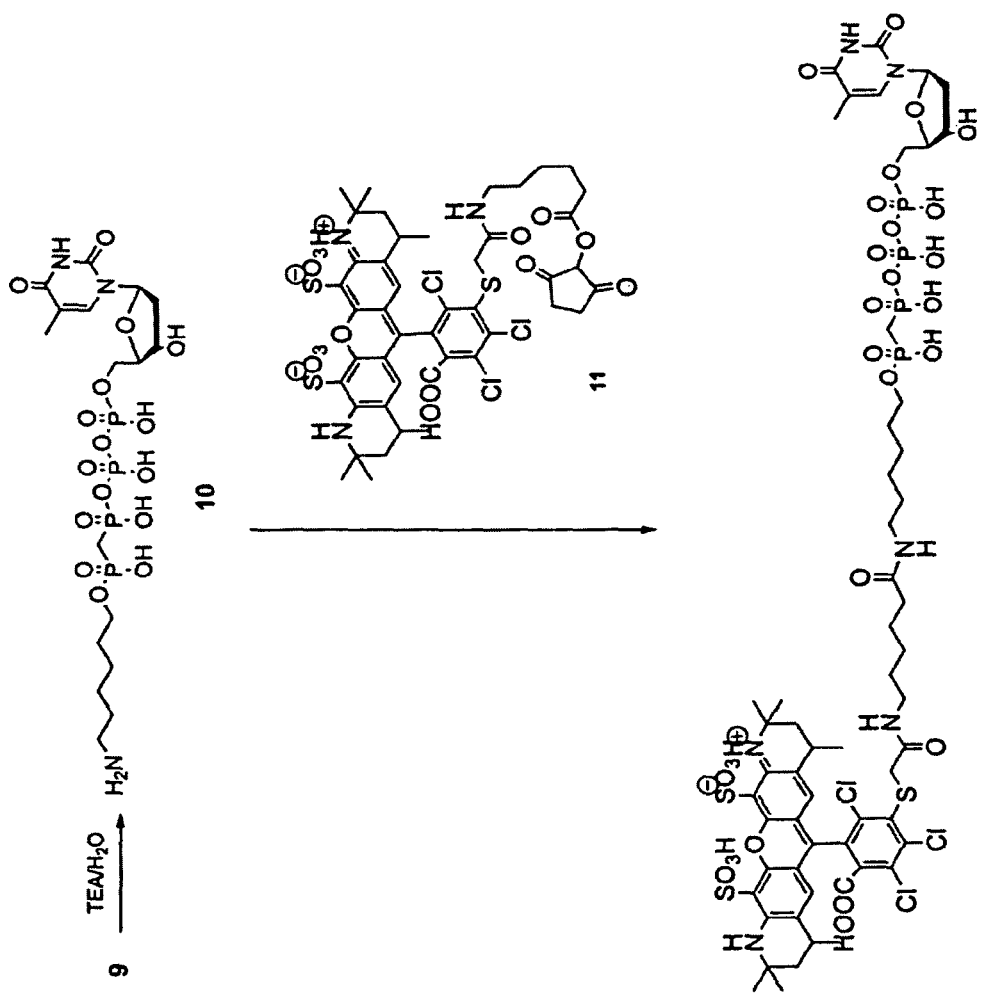

The synthetic scheme for this compound is illustrated in FIGS. 2A, 2B and 2C. To a stirred solution of methylenebis (phosphonic dichloride) 4 (50 mg, 0.2 mmol) in triethylphosphate (2 mL) in an ice-water bath was added solid 6-(Fmoc-amino)-1-hexanol 3 (See FIG. 2A). The reaction was allowed to warm to room temperature and was stirred under argon overnight. The reaction was quenched by adding TEAB solution (1.0 M, 1 mL) followed by adding triethylamine to adjust to pH 8. The phosphonate 5 was isolated by AE-HPLC (solvent A: 0.04 M TEAB with 20% acetonitrile, solvent B: 0.8 M TEAB with 20% acetonitrile) followed by RP-HPLC.

Thymidine diphosphate tributylammonium salt 6 (10 μmol, converted from sodium salt) was dried by co-evaporating with acetonitrile two times and was dissolved in anhydrous dimethylformamide (0.5 mL). Solid 1,1'-carbonyldiimidazole 7 (8.1 mg, 50 μmol) was added and the reaction was stirred under argon at room temperature for 5 hrs. Methanol (3.24 uL, 80 μmol) was added and the reaction mixture was stirred for 30 min to give a solution of the activated phosphodiester 8. In a separate flask, a solution of phosphonate 5 (10 μmol) was dried down by roto-evaporation followed by co-evaporation with acetonitrile 2 times. The solution of 8 was added to the flask containing 5, and the reaction mixture was stirred under argon at room temperature for 40 hours. The reaction mixture was diluted with 20 mL of water and was purified by RP-HPLC to give compound 9 (See FIG. 2B).

The compound 9 was dissolved in water (1 mL) and was added triethylamine (65 μL). The reaction mixture was stirred under argon at room temperature for 19 hrs. The mixture was diluted with water (4 mL) and was extracted with ethyl acetate (3×10 mL) to remove by-products. The aqueous layer was evaporated to dryness to give amino-hexyl-phosphonate 10 that was used without further purification.

The amino-hexyl-phosphonate 10 (0.82 μmol) in 130 μL of water was added to a vial containing Alexa 546 NHS ester 11 (1.0 mg, Invitrogen), and the vial was vortexed briefly. Sodium bicarbonate solution (10 μL, 0.3 M) was added. The reaction mixture was vortexed briefly and was placed in the dark at room temperature for 1 hr. An additional sodium bicarbonate solution (15 μL, 0.3 M) was then added, and the reaction was allowed to proceed for another 2 hrs. The reaction mixture was purified by AE-HPLC followed by RP-HPLC to afford the product A546-phosphonate-thymidine 1 (0.51 μmol, 62% yield) (See FIG. 2C).

3. Methylene Phosphonate 3

Figure 3:
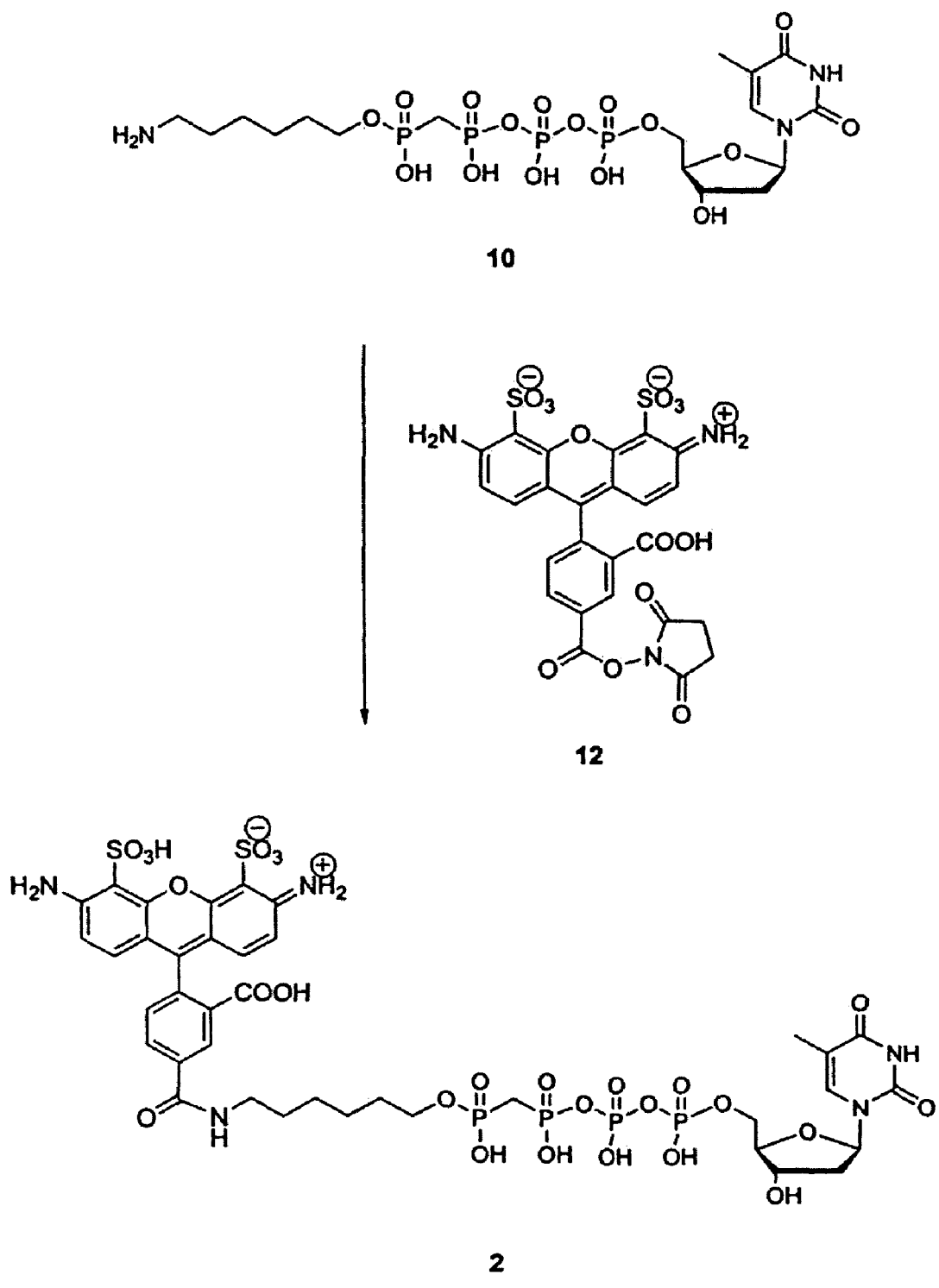
FIG. 3 shows a synthetic scheme for producing another exemplary compound of the invention.

A third methylene phosphonate (A488-phosphonate-thymidine 2) was synthesized incorporating the methylene linkage between the γ and δ phosphorus groups but including an AAlexa488 dye group, and having the following formula:

The synthetic scheme for this compound is illustrated in FIG. 3. The amino-hexyl-phosphonate 10 (0.5 μmol) in 0.5 mL of water was added to a vial containing Alexa 488 TFP ester 12 (1.0 mg, Invitrogen), and the vial was vortexed briefly to dissolve the dye. Sodium bicarbonate solution (0.3 M, 17 μL) was added. The reaction was vortexed briefly and was allowed to proceed at room temperature. After 1 hr, an additional amount of sodium bicarbonate solution (0.3 M, 100 μL) was added, and the reaction was allowed to proceed for an additional two hours. The reaction mixture was then purified by RP-HPLC to afford A488-phosphonate-thymidine 2 (0.28 μmol, 56%).

Example 2

Incorporation of Analogs into DNA, by DNA Polymerases

Each of the compounds synthesized in Example 1 were subjected to experiments to determine whether they could be processed by DNA polymerases, and particularly a mutated derivative of Φ29 DNA polymerase, having reduced exonucleoase activity relative to the wild type Φ29 polymerase. The experiment focused on the bulk incorporation of analogs during template dependent synthesis, by substituting the nucleotide analog for one type of nucleotide in the synthesis, in these examples, substituting a T analog for the naturally occurring thymidine.

The Phi29 DNA polymerase mutant N62D was preincubated with DNA template (72 nucleotide circular DNA including repetitive sequence AGTC) with annealed DNA primer, the preincubation mix includes composition of three native nucleosides (dCTP, dATP and dGTP) and one of the listed analogs (2-5), the control reaction includes four native nucleotides (dNTP). After a short preincubation the reaction was started with $MnCl_2$ and incubated for 1 hour at 30° C. The reactions were each loaded and separated in separate lanes of a 0.6% agarose gel in TE Buffer, and the resulting gel was stained with Syber Gold and visualized on a Typhoon scanner. In this assay, incorporation of the compounds 1, 2 and 3 was similar to the reaction with four native nucleotides.

Figure 4:
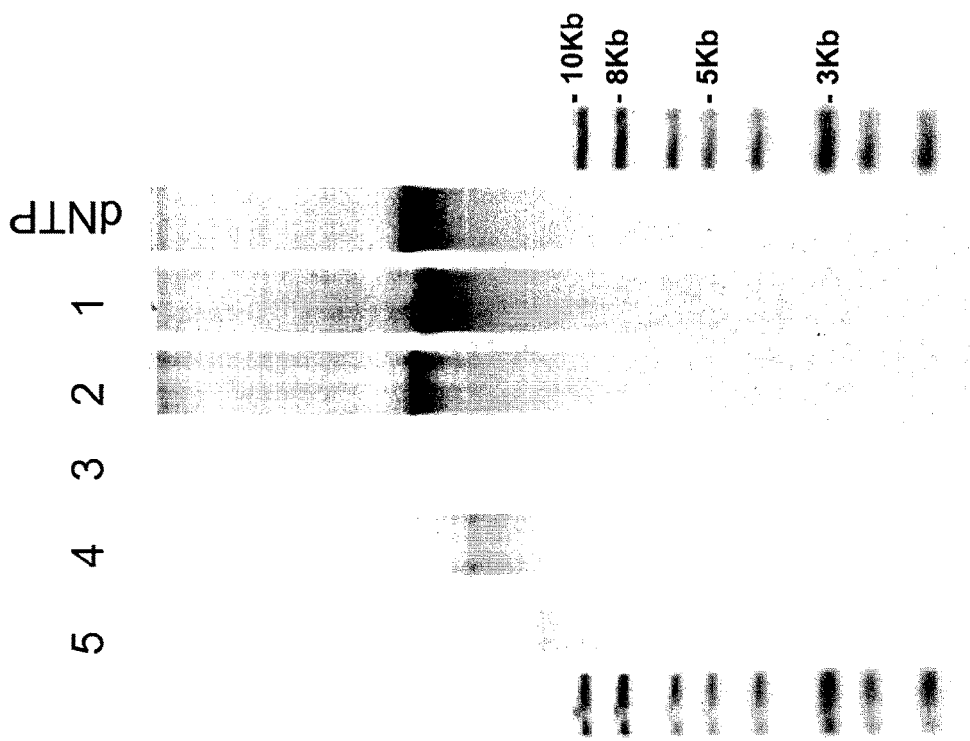
FIG. 4 shows an image of an agarose gel illustrating incorporation of the compounds of the invention in a template dependent polymerization reaction by a DNA polymerase.
Figure 4:
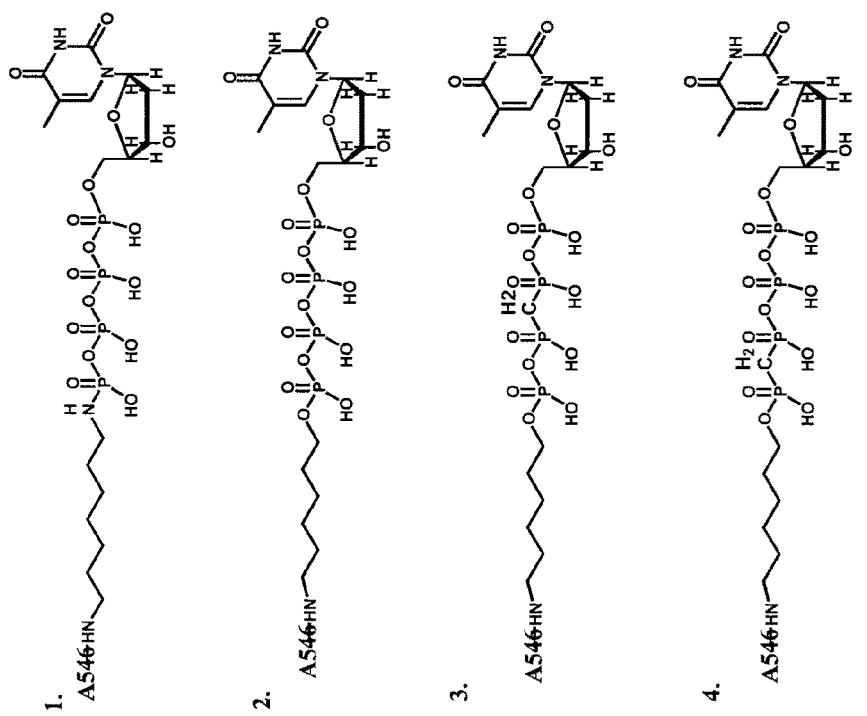

FIG. 4 shows an image of an agarose gel of the polymerization products of each reaction. In particular, the extreme side lanes included size standards that are identified along side the gel. The lane labeled "dNTP" included a control

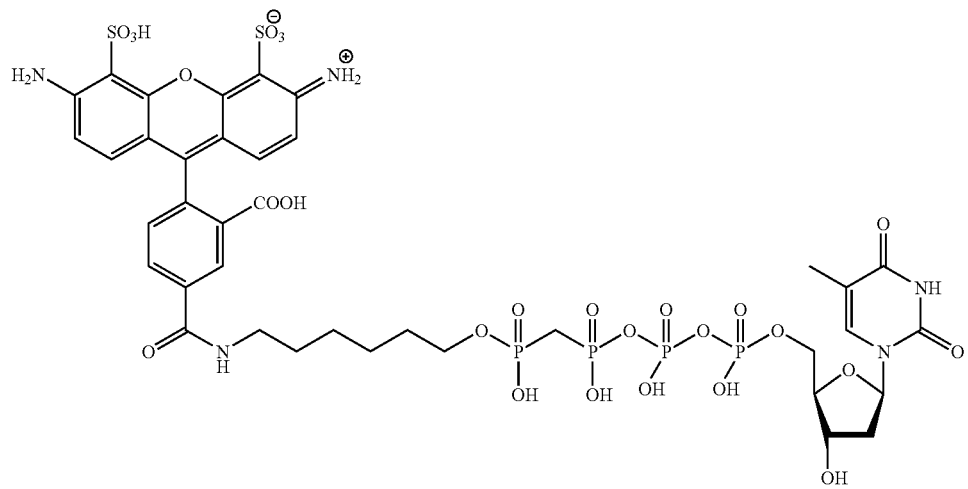

experiment that utilized only conventional nucleoside triphosphates, including dTTP. Lane 1 utilized a thymidine tetraphosphate analog labeled with an Alexa 546 dye through an amidate linkage, in place of dTTP. Lane 2 included a similar compound but wherein the dye was coupled to the analog through an ester linkage. Lanes 3 and 4 each included the polymerase reaction product using only the methylene phosphonate analogs shown produced in Examples 1 and 2, above, respectively, as the T analog, respectively. Lane 5 included the analog from Example 2, above, that incorporated an Alexa488 dye in place of the Alexa546 dye used in the other compounds. The compounds used in each polymerization reaction are listed next to the gel image.

As can be seen from the gel, each of methylene phosphonate compounds were readily incorporated into the synthesized DNA and with sufficient processivity as to result in relatively long strand lengths for the products. Specifically, each product seen in the gel is roughly at or above 10 kB in length, indicating that the presence of the analogs does not significantly interrupt the enzyme's processivity.

Figure 5A:
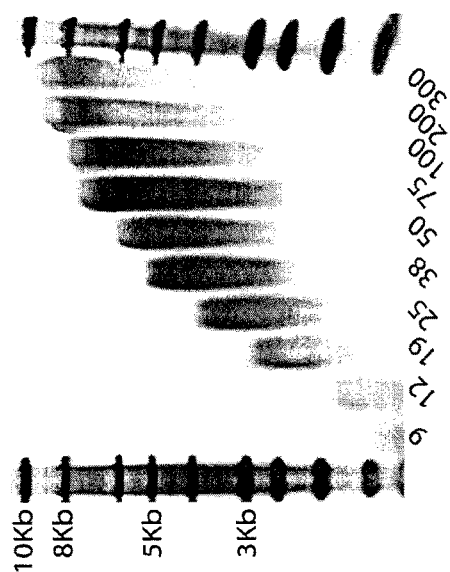
FIG. 5 shows template dependent incorporation of compounds of the invention as dependent upon compound concentration.
Figure 5B:
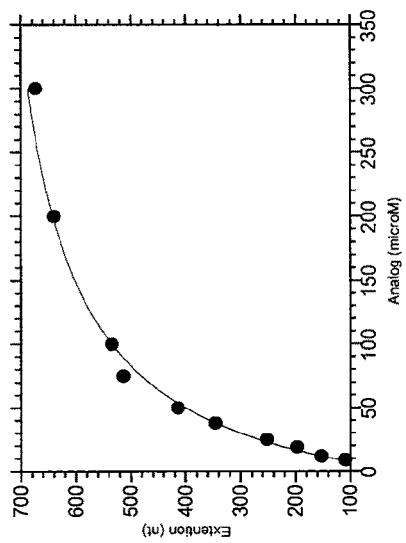

FIG. 5 shows effect of the compound (No. 4. from FIG. 4) concentration on a template dependent polymerization rate. The reaction condition was similar to the reaction from FIG. 4. With respect to FIG. 5A indicated at the bottom of the figure is the compound concentration (microM). FIG. 5B shows a quantitative representation of the results from FIG. 5A. Each data point represents an average length of the DNA generated with DNA polymerase at an individual compounds concentration. The results were fitted with hyperbola.

Although described in some detail for purposes of illustration, it will be readily appreciated that a number of variations known or appreciated by those of skill in the art may be practiced within the scope of present invention. All terms used herein are intended to have their ordinary meaning unless an alternative definition is expressly provided or is clear from the context used therein. To the extent any definition is expressly stated in a patent or publication that is incorporated herein by reference, such definition is expressly disclaimed to the extent that it is in conflict with the ordinary meaning of such terms, unless such definition is specifically and expressly incorporated herein, or it is clear from the context that such definition was intended herein. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes.

What is claimed is:

1. A composition comprising a labeled nucleoside polyphosphate, wherein said nucleoside polyphosphate comprises at least one phosphonate linkage in the phosphorous containing chain of said nucleoside polyphosphate.

2. The composition of claim 1, wherein said phosphonate linkage is a substituted or unsubstituted alkyl group.

3. The composition of claim 1, wherein said nucleoside polyphosphate is a nucleoside triphosphate.

4. The composition of claim 1, wherein said nucleoside polyphosphate is a nucleoside tetraphosphate.

5. The composition of claim 1, wherein said nucleoside polyphosphate is a nucleoside pentaphosphate.

6. The composition of claim 1, wherein said nucleoside polyphosphate is a nucleoside hexaphosphate.

7. A composition comprising a nucleoside polyphosphate, wherein said nucleoside polyphosphate comprises the structure:

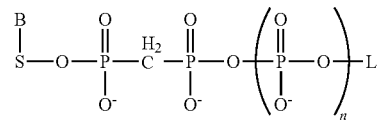

wherein
B is a natural or non-natural nucleobase;
L is a detectable label;
S is selected from a sugar moiety, an acyclic moiety and a carbocyclic moiety; an
n is an integer from 1 to 4.

8. The composition of claim 1, wherein said nucleoside polyphosphate comprises the structure:

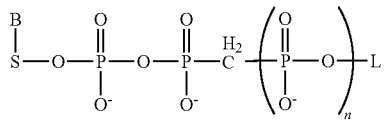

wherein
B is a natural or non-natural nucleobase;
L is a detectable label;
S is selected from a sugar moiety, an acyclic moiety and a carbocyclic moiety; an
n is an integer from 1 to 4.

9. A composition comprising a nucleoside polyphosphate, wherein said nucleoside polyphosphate comprises the structure:

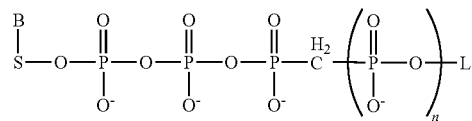

B is a natural or non-natural nucleobase;
L is a detectable label;
S is selected from a sugar moiety, an acyclic moiety and a carbocyclic moiety; an
n is an integer from 1 to 3.

* * * * *